US012629124B2

(12) United States Patent
Xiang et al.

(10) Patent No.: US 12,629,124 B2
(45) Date of Patent: May 19, 2026

(54) MULTI-MODALITY AND MULTI-SCALE FEATURE AGGREGATION FOR SYNTHESIZING SPECT IMAGE FROM FAST SPECT SCAN AND CT IMAGE

(71) Applicant: Subtle Medical, Inc., Menlo Park, CA (US)

(72) Inventors: Lei Xiang, Shanghai (CN); Enhao Gong, Sunnyvale, CA (US)

(73) Assignee: Subtle Medical, Inc., Menlo Park, CA (US)

( * ) Notice: Subject to any disclaimer, the term of this patent is extended or adjusted under 35 U.S.C. 154(b) by 104 days.

(21) Appl. No.: 18/512,709

(22) Filed: Nov. 17, 2023

(65) Prior Publication Data
US 2024/0307018 A1     Sep. 19, 2024

Related U.S. Application Data

(63) Continuation of application No. PCT/CN2022/097596, filed on Jun. 8, 2022, which is
(Continued)

(51) Int. Cl.
*A61B 8/00* (2006.01)
*A61B 6/00* (2006.01)
(Continued)

(52) U.S. Cl.
CPC ............ *A61B 6/5235* (2013.01); *A61B 6/032* (2013.01); *A61B 6/037* (2013.01); *A61B 6/5217* (2013.01);
(Continued)

(58) Field of Classification Search
CPC ......... A61B 6/032; A61B 6/037; A61B 6/505; A61B 6/5217; A61B 6/5235;
(Continued)

(56) References Cited

U.S. PATENT DOCUMENTS

2018/0240219 A1     8/2018     Mentl et al.
2019/0101605 A1     4/2019     Hyun et al.
(Continued)

FOREIGN PATENT DOCUMENTS

CN     111161182 A     5/2020
CN     111867474 A     10/2020
(Continued)

OTHER PUBLICATIONS

PCT/CN2022/097596 International Preliminary Report on Patentability dated Aug. 25, 2022.
(Continued)

*Primary Examiner* — Mark D Remaly
(74) *Attorney, Agent, or Firm* — Wilson Sonsini Goodrich & Rosati

(57)     ABSTRACT
A computer-implemented method is provided for improving image quality. The method comprises: acquiring, using single-photon emission computed tomography (SPECT), a medical image of a subject, wherein the medical image is acquired with shortened acquisition time; and applying a deep learning network model to the medical image to generate an enhanced medical image.

18 Claims, 8 Drawing Sheets

Related U.S. Application Data a continuation of application No. PCT/CN2021/099142, filed on Jun. 9, 2021.

(51) Int. Cl.

| | |
|---|---|
| *A61B 6/03* | (2006.01) |
| *G06T 5/50* | (2006.01) |
| *G06T 5/60* | (2024.01) |
| *A61B 6/50* | (2024.01) |

(52) U.S. Cl.
CPC .............. *A61B 6/5258* (2013.01); *G06T 5/50* (2013.01); *G06T 5/60* (2024.01); *A61B 6/505* (2013.01); *G06T 2207/10081* (2013.01); *G06T 2207/10108* (2013.01); *G06T 2207/20081* (2013.01); *G06T 2207/20084* (2013.01)

(58) Field of Classification Search
CPC ................. A61B 6/5258; G01T 1/161; G06T 2207/10081; G06T 2207/10108; G06T 2207/20081; G06T 2207/20084; G06T 5/50; G06T 5/60
See application file for complete search history.

(56) References Cited

U.S. PATENT DOCUMENTS

| | | | |
|---|---|---|---|
| 2019/0365341 A1 | 12/2019 | Chan et al. | |
| 2022/0327665 A1* | 10/2022 | Chan ...................... | G06N 3/084 |

FOREIGN PATENT DOCUMENTS

| | | |
|---|---|---|
| CN | 112351739 A | 2/2021 |
| CN | 112770838 A | 5/2021 |

OTHER PUBLICATIONS

PCT/CN2022/097596 International Search Report and Written Opinion dated Aug. 25, 2022.

* cited by examiner 101             103             105

CT            1/7 SPECT            Standard SPECT

MULTI-MODALITY AND MULTI-SCALE FEATURE AGGREGATION FOR SYNTHESIZING SPECT IMAGE FROM FAST SPECT SCAN AND CT IMAGE

CROSS-REFERENCE TO RELATED APPLICATION

This application is a continuation of PCT International Application No. PCT/CN2022/097596 filed on Jun. 8, 2022, which claims priority to PCT International Application No. PCT/CN2021/099142 filed on Jun. 9, 2021, the content of which is incorporated herein in its entirety.

BACKGROUND

Single-photon emission computed tomography (SPECT) is a nuclear medicine tomographic imaging technique using gamma rays. A SPECT scan monitors level of biological activity at each place in a 3-D region analyzed. Similar to conventional nuclear medicine planar imaging using a gamma camera, before a scan, a radioactive tracer (e.g., gamma-emitting radioisotope (a radionuclide)) is injected into the patient, the emissions from the radionuclide indicate is then captured by a gamma camera of the SPECT system.

However, standard acquisition time for one SPECT image can be long (e.g., about 20 min/bed) which is uncomfortable and intolerable for patients to hold still in the scanner. Undesirable imaging artifacts as well as misplacement of events in space may appear due to the long scan time and the undesired movement of patient during the scan. The lengthy exam time may also make the procedure uncomfortable for patients who have difficulty staying still. Such long scan time for SPECT exams may result in high imaging cost and limit the patient volume and accessibility. Additionally, reducing the acquisition time may amplify noise and inevitably degrade the image quality, thus hampering clinical interpretation of SPECT images.

SUMMARY

A need exists for shortening the acquisition time of SPECT to improve patient's experience, reduce examination costs, and reduce the likelihood of patient motion during scanning without compromising the quality of SPECT images. The present disclosure provides improved single-photon emission computed tomography (SPECT) systems and methods that can address various drawbacks of conventional systems, including those recognized above. Methods and systems of the presenting disclosure capable of providing improved image quality or preserving image quality with shortened image acquisition time. Method and system of the presenting disclosure provide SPECT imaging with shortened image acquisition time without compromising image quality.

Single-photon emission computed tomography can be combined with imaging modalities. For example, SPECT coupled with computed tomography (SPECT/CT) is an important and accurate diagnostic measurement. For example, SPECT/CT techniques may provide accurate information for distinguishing prostate cancer bone metastases from spinal and pelvic osteoarthritic lesions. Such SPECT/CT imaging may also be improved by the presented methods and systems by shortening the acquisition time without degrading the image quality.

Traditionally, short scan duration may result in low image quality. The provided methods and systems may significantly reduce SPECT scan time by applying deep learning techniques so as to mitigate imaging artifacts and improve image quality. Examples artifacts in medical imaging may include noise (e.g., low signal noise ratio), blur (e.g., motion artifact), shading (e.g., blockage or interference with sensing), missing information (e.g., missing pixels or voxels in painting due to removal of information or masking), and/or reconstruction (e.g., degradation in the measurement domain).

The present disclosure provides an acceleration method employing deep learning techniques to improve the image quality acquired with shortened acquisition time (i.e., fast scan). In some cases, the deep learning techniques may comprise using multi-modality and multi-scale feature aggregation-based framework to generate SPECT images from a fast scan with image quality comparable to SPECT images acquired with standard acquisition time (e.g., slow scan) or long acquisition time. This beneficially accelerates SPECT image acquisition by an acceleration factor of at least 1.5, 2, 3, 4, 5, 6, 7, 8, 9, 10, 15, 20, a factor of a value above 20 or below 1.5, or a value between any of the two aforementioned values. For example, the fast scan SPECT images can be acquired with only $1/7$ acquisition time or faster without compromising the image quality.

In some embodiments, the provided method may utilize the associated features between a fast SPECT scan and corresponding CT image to improve anatomy structural boundary and overall image quality. Including CT image as the input of network beneficially provides a clear anatomy features resulting in clear boundary in the synthesized standard SPECT image. The term "standard SPECT image" as utilized herein generally refers to SPECT image acquired with standard acquisition time.

Additionally, the provided method may allow for faster SPECT imaging acquisition while preserving quantification accuracy related to physiological or biochemical information. For example, methods and systems of the present disclosure may provide accelerated SPECT image acquisition while preserving accuracy in standardized uptake quantification. The quantification accuracy may be preserved or improved over the fast scan SPECT image by boosting the image contrast and the accuracy (e.g., standardized uptake value (SUV) in lesion regions. The SPECT image acquisition can be accelerated by an acceleration factor of at least 1.5, 2, 3, 4, 5, 6, 7, 8, 9, 10, 15, 20, a factor of a value above 20 or below 1.5, or a value between any of the two aforementioned values. The term "fast scan SPECT image" may generally refer to a SPECT image acquired under shortened acquisition time at an acceleration factor of a value greater than 1. The standard acquisition time is at least 1, 2, 3, 4, 5, 6, 7, 8, 9, 10, 15, 20 times of the shortened acquisition time of the fast scan SPECT image.

The method herein may boost the image contrast and the accuracy (e.g., standardized uptake value (SUV) in lesion regions by penalizing the losses in these regions such as utilizing corresponding lesion attention map.

In an aspect, a computer-implemented method is provided for improving image quality. The method comprises: acquiring, using single-photon emission computed tomography (SPECT), a first medical image of a subject, wherein the first medical image is acquired with shortened acquisition time; combining the medical image with a second medical image acquired using computed tomography (CT) to generate an input image; and applying a deep learning network model to the input image and outputting an enhanced medical image. The enhanced medical image has an image quality same as a SPECT image acquired with an acquisition time longer than the shortened acquisition time combined with a corresponding CT image or has a quantification accuracy improved over the first medical image.

In some embodiments, the deep learning network model comprises a U²-Net architecture. in some cases, the U²-Net architecture comprises a plurality of residual blocks with different sizes. In some cases, an output generated by a decoder stage of the U²-Net architecture is fused with the input image to generate the enhanced medical image.

In some embodiments, the deep learning network model is trained using training data comprising a SPECT image acquired using shortened acquisition time, a corresponding CT image and a SPECT image acquired using a standard acquisition time. In some embodiments, the quantification accuracy is improved by training deep learning network model using a lesion attention mask. In some cases, the lesion attention mask is included in a loss function of the deep learning network model. In some cases, the lesion attention mask is generated from a SPECT image acquired using shortened acquisition time in the training data. For example, the lesion attention mask is generated by filtering the SPECT image acquired using shortened acquisition time with a standardized uptake value (SUV) threshold.

In some embodiments, the first medical image and the second medical image are acquired using a SPECT/CT scanner. In some embodiments, the enhanced medical image has an improved signal-noise ratio.

In a related yet separated aspect, a non-transitory computer-readable storage medium including instructions that, when executed by one or more processors, cause the one or more processors to perform operations. The operations comprise: acquiring, using single-photon emission computed tomography (SPECT), a first medical image of a subject, wherein the first medical image is acquired with shortened acquisition time; combining the medical image with a second medical image acquired using computed tomography (CT) to generate an input image; and applying a deep learning network model to the input image and outputting an enhanced medical image, where the enhanced medical image has an image quality same as a SPECT image acquired with an acquisition time longer than the shortened acquisition time combined with a corresponding CT image or has a quantification accuracy improved over the first medical image.

In some embodiments, the deep learning network model comprises a U²-Net architecture. in some cases, the U²-Net architecture comprises a plurality of residual blocks with different sizes. In some cases, an output generated by a decoder stage of the U²-Net architecture is fused with the input image to generate the enhanced medical image.

In some embodiments, the deep learning network model is trained using training data comprising a SPECT image acquired using shortened acquisition time, a corresponding CT image and a SPECT image acquired using a standard acquisition time. In some embodiments, the quantification accuracy is improved by training deep learning network model using a lesion attention mask. In some cases, the lesion attention mask is included in a loss function of the deep learning network model. In some cases, the lesion attention mask is generated from a SPECT image acquired using shortened acquisition time in the training data. For example, the lesion attention mask is generated by filtering the SPECT image acquired using shortened acquisition time with a standardized uptake value (SUV) threshold.

In some embodiments, the first medical image and the second medical image are acquired using a SPECT/CT scanner. In some embodiments, the enhanced medical image has an improved signal-noise ratio.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and descriptions are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Figure 1:
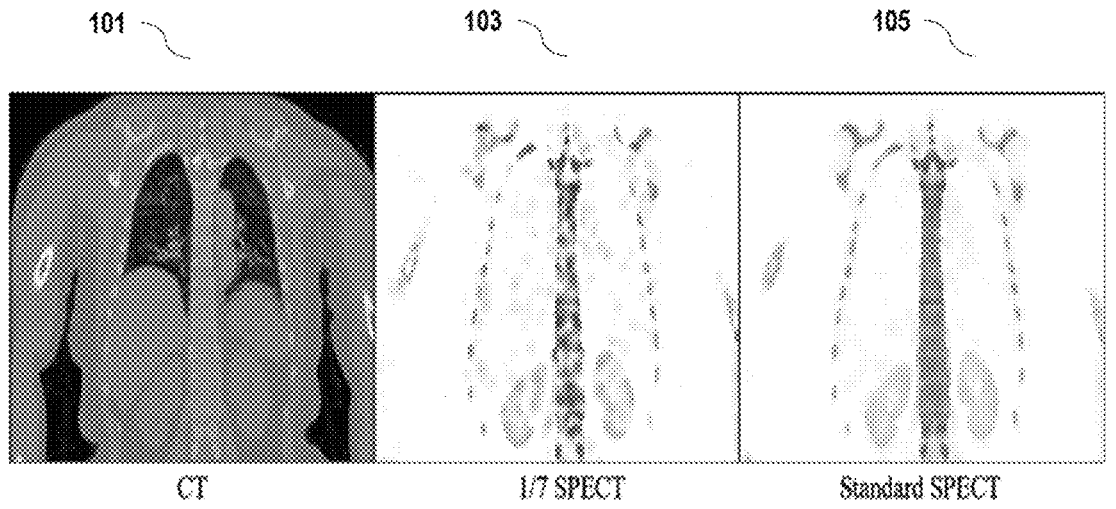
FIG. 1 shows an example of a fast scan SPECT image acquired with shortened acquisition time.

Short scan duration may result in low image quality. The image quality of the SPECT image as described herein may include general image quality (e.g., signal noise ratio, resolution, etc.), detail of radiotracer (e.g., 99mTc-MPD) distribution, presence of artifacts and/or general diagnostic confidence. FIG. 1 shows an example of a fast scan SPECT image acquired with 1/7 standard acquisition time or faster. In the example, the fast scan SPECT images 103 and corresponding CT image 101 are acquired by a SPECT/CT. The fast SPECT scan is acquired with 1/7 standard acquisition time (referred to as ⅐ SPECT 103). Compared to the standard SPECT 105 (SPECT acquired with standard time such as about 20 min/bed), the fast scan SPECT has a degraded image quality (e.g., greater noise and artifacts, less detail of the radiotracer distribution).

The provided methods and systems may significantly reduce SPECT scan/acquisition time by applying deep learning techniques so as to mitigate imaging artifacts and improve image quality. The present disclosure provides an imaging acceleration method employing deep learning techniques to improve the image quality acquired with shortened acquisition time (i.e., fast scan). In some cases, the deep learning techniques may comprise using multi-modality and multi-scale feature aggregation-based framework to generate SPECT images from a fast scan with image quality comparable to SPECT images acquired with standard acquisition time (e.g., standard SPECT). This beneficially accelerates SPECT image acquisition by an acceleration factor of at least 1.5, 2, 3, 4, 5, 6, 7, 8, 9, 10, 15, 20, a factor of a value above 20 or below 1.5, or a value between any of the two aforementioned values. The provided method and systems can achieve a shortened acquisition time of no more than ⅕, ⅙, ⅐, ⅛, ⅑, ⅒ of the standard acquisition time.

SPECT imaging can be combined with other imaging modalities to provide imaging in different applications. For example, single-photon emission computed tomography coupled with computed tomography (SPECT/CT) plays a pivotal role for differential diagnosis such as for diagnosis of benign and malignant bone lesions. In the SPECT/CT hybrid imaging, images from the two different types of scans are combined together. For instance, a SPECT gamma scanner may be built to operate with a conventional CT scanner, with coregistration of images.

The combined SPECT/CT scan can provide precise information about how different parts of the body are working and more clearly identify problems. For example, reconstruction algorithms have been developed in bone hybrid imaging (SPECT/CT) scanner. Different from classic SPECT reconstructions, such reconstruction algorithms may utilize an ordered subset conjugate gradient minimization algorithm (OSCGM) for image reconstruction. This construction algorithm can provide SPECT images with bone anatomy appearance as a CT-based tissue segmentation is incorporated into SPECT reconstruction and also provide a quantitative reconstruction. Such progress of image acquisition and reconstruction could convey a higher diagnostic confidence through an enhanced bone uptake location. However, patient is still exposed to additional radiation exposure in terms of effective dose incurred in the CT portion of SPECT/CT examinations.

Although recent advances in hardware (e.g., cameras and collimators) and software (e.g., reconstruction algorithms incorporating noise regularization and resolution recovery) may facilitate reducing scanning time and/or injected activity. Shortening the acquisition time may still degrade the image quality. As show in FIG. 1, a pair of SPECT and CT images are acquired using a SPECT/CT system or scanner. The fast scan SPECT (e.g., ⅐ SPECT) has low image quality due to the fast scan.

Methods and systems herein may effectively reduce the radiation exposure by shortening the SPECT/CT examination time (e.g., shorten the SPECT scan time) without comprising the quality of the output image. In some embodiments, systems and methods herein may synthesize an enhanced medical image from the fast scan SPECT image and CT image and the enhanced medical image has an image quality same as a SPECT image acquired with standard acquisition time combined with a corresponding CT image. In some embodiments, the enhanced medical image may have an image quality improved over the fast scan SPECT image in terms of quantification accuracy. For example, the provided method may utilize the associated features between a fast SPECT scan and corresponding CT image to improve anatomy structural boundary and the overall image quality.

In some embodiments, the provided method may allow for faster SPECT imaging acquisition while preserving quantification accuracy related to physiological or biochemical information. For example, methods and systems of the present disclosure may provide accelerated SPECT image acquisition while preserving accuracy in standardized uptake quantification. The method herein may preserve or improve the quantification accuracy by boosting the image contrast and the accuracy (e.g., standardized uptake value (SUV) in lesion regions. In some cases, the image contrast and accuracy in lesion regions may be preserved by penalizing the losses in these regions such as utilizing an attention map. The attention map may comprise an attention feature map or ROI attention masks. The attention map may comprise information about a lesion attention map or other attention map that comprises clinically meaningful information. For example, the attention map may comprise information about regions where particular tissues/features are located. For example, the proposed method can effectively suppress the noise texture in the fast-scanned SPECT image and recover clear anatomy structural details, especially SUV value in the lesion regions, which is comparable to SPECT image quality using standard acquisition time.

The deep learning framework of the present disclosure may combine rich features from both a fast SPECT image and its corresponding CT image to predict a synthetized SPECT image with improved quality. In embodiments, the deep learning framework may be based on U²-Net architecture which can integrate multi-scale and multi-modality features from both an accelerated scanning (e.g., ⅐ SPECT) image and a corresponding CT image. In some embodiments, the provided method may also incorporate a lesion attention loss function to enhance sensitivity of the deep learning model to reconstruct lesion regions with more accurate SUV measures.

The method herein may also be capable of quantitatively evaluating the image quality and performance of the model. For example, quantitative image quality metrics such as normalized root-mean-squared-error (NRMSE), peak signal to noise ratio (PSNR), and structural similarity (SSIM) may be calculated for the enhanced and non-enhanced accelerated SPECT scans, where higher image quality is represented by higher PSNR and/or SSIM. Other suitable image quality quantification metrics may also be utilized to quantify the image quality.

Methods and Deep Learning Framework

Figure 2:
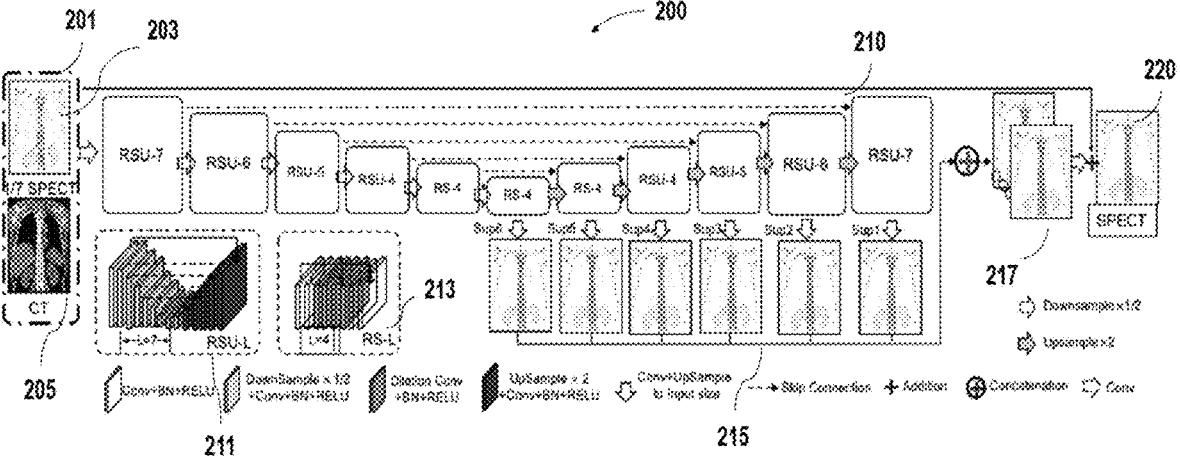
FIG. 2 shows an example of a deep learning framework to synthesize SPECT image from fast scanned SPECT image and the corresponding CT image.

FIG. 2 shows an example of a deep learning framework 200 to synthesize SPECT image 220 from fast scanned SPECT image 203 and the corresponding CT image 205. The provided method applies a U²-Net framework 200 to integrate multi-scale features from these two different modality images 203, 205 as shown in FIG. 2. The deep learning framework 200 may comprise a unique residual U-block and a U²-Net architecture built with this block. The provided method may also utilize improved loss functions to train the model, along with attention loss (e.g., lesion attention loss) to improve the accuracy (e.g., SUV) and the deep supervision strategy that helps the training to converge smoothly.

Combination of Fast Scan SPECT and CT

In some embodiments, the input data 201 may comprise a pair of SPECT image 203 and CT image 205. The input data 201 may be a combined image of the SPECT image 203 and CT image 205. For instance, the output of a SPECT/CT scan including the combined SPECT image and CT image may be used as the input to the deep learning model. The fast scan SPECT image and the CT image may be combined such as by registration of CT and SPECT images to bring these images into spatial alignment. After registration, fusion of SPECT and CT images may be performed to combine the functional information from SPECT with the anatomical information from CT.

The SPECT image and CT image may be acquired simultaneously. For example, the SPECT image and CT image may be acquired by a SPECT/CT scanner. The simultaneous SPECT and CT acquisition mode of the SPECT/CT scanner may facilitate the integration of input data from the two modalities which will be described later herein. The CT images 205 may provide complementary anatomical information for depicting detailed high-resolution features that might be missed if only the fast SPECT images were used as input. The provided method may combine the fast scan SPECT image (e.g., 1/7 SPECT image 203) and the corresponding CT image 205 as the input data 201. The input data 201 may then be processed by the framework 210 built with residual U-blocks and U²-Net.

During a training stage, the training dataset may include the input data (including the combined fast scan SPECT and CT image) paired the standard SPECT image as ground truth data. In some cases, the ground truth data may be acquired by a SPECT scan with standard acquisition time combined with the corresponding CT image i.e., standard SPECT/CT image acquired with the simultaneous SPECT and CT acquisition mode of the SPECT/CT scanner.

Residual U-Blocks and U²-Net

Processing the combination of SPECT and CT images using the provided U²-Net architecture can beneficially preserve both local and global contextual features. The neural network architecture of U²-Net is different from conventional CNN designs. Unlike conventional CNN networks which usually use small convolutional filters (e.g., size of 1×1 or 3×3) to extract features, U²-Net is a simple and powerful deep network architecture containing a novel two-layer nested U-shaped structure.

The U-net architecture 210 is essentially a multi-scale encoder-decoder architecture, with skip-connections that forward the output of each of the encoder layers directly to the input of the corresponding decoder layers. The residual connection between the input images 201 and the output image 220 is introduced to accelerate the training process.

The U-net architecture 210 may comprise one or more functional blocks including a Residual U-block (RSU) 211. An RSU block may comprise a mixture of receive domains of variable sizes that help capture contextual information on different scales efficiently. An RSU block may comprise a plurality of convolutional layers. In most layers, the outputs of its convolutional layers are followed by point-wise ReLU activation functions ReLU(•)=max(•, 0). An RSU block may comprise a plurality of components including an input convolutional layer, U-Net-like symmetric encoder-decoder structure of 'L' height, and a residual connection to fuse local and multi-scale features (e.g., by using summation).

At training time, batch normalization layers (BN) are placed between the convolutional and ReLU layers. At evaluation time, the batch normalization layers may be removed, and replaced by an affine layer that applies the learned normalization. The RSU block may use pooling operations to increase the overall architecture depth without significantly affecting the computational cost.

The U²-Net architecture 210 as shown in the example comprises an encoder (e.g., a 6-stage encoder), a decoder (e.g., 5-stage decoder), and a graph fusion module attached to the decoders at different stage. The U²-Net based framework is capable of extracting both local and global information from multi-scale features obtained by the plurality of RSU blocks. As illustrated in the example, in the encoder stages, a plurality of RSU blocks 211 (e.g., RSU-7, RSU-6, RSU-5, RSU-4 where '7', '6', '5' and '4' denote the heights (L) of the RSU blocks) of variable heights/size are used respectively to extract the feature maps. The plurality of RSU blocks with the multiple different sizes beneficially provide contextual information from different scales for improving the accuracy of the features (e.g., anatomical structural details).

As the resolution of feature maps in the middle part of U²-Net are relatively low, further down-sampling of these feature maps may cause loss of useful context. The provided framework may use dilated convolutions in the decoder stage to replace the pooling and upsampling operations so as to preserve the contextual information. Dilated Convolutions may expand a kernel by inserting defined gaps/holes between the kernel elements. In the decoder stages, one or more functional blocks 213 (e.g., 'RS-L' with height L=4) may be included. Such functional block (e.g., RS-4) may have similar structures to the symmetrical encoder stages. The decoder may comprise a plurality of decoder stages (e.g., 5 stages in total) in which each decoder stage may take the concatenation of the upsampled feature maps from its previous stage and the feature maps from its symmetrical encoder stage as the input as shown in FIG. 2.

The last graph fusion module of the framework may be used for generating the final synthesized SPECT images 220. The U²-Net framework may generate a plurality of side output synthesized SPECT images $$S_{side}^{(6)}, S_{side}^{(5)}, S_{side}^{(4)}, S_{side}^{(3)}, S_{side}^{(2)}, S_{side}^{(1)}$$

215, which are upsampled to have the same size as the input image 201. These side output synthesized SPECT images 215 may be generated by the plurality of decoder stages respectively. Next, the plurality of side output synthesized SPECT images 215 may be fused such as by a concatenation operation and inputting to a convolution layer (e.g., 1*1 convolution layer) 217. The framework may then generate the final synthesized SPECT image 220 by a long skip connection with the input fast-scan SPECT image (e.g., 1/7 SPECT 203).

Lesion Attention Loss and Deep Supervision

The method herein may be capable of preserving the accuracy of the image by including an attention map. For example, to ensure the accuracy and sharpness of the synthesized SPECT image and important regions of interest (ROIs), a loss function with combination of structural similarity (SSIM) loss $L_{SSIM}$ and $L_1$ loss (i.e., $L_1$ norm loss) may be utilized. Below is an example of the loss function:

$$L = L_1 + \alpha L_{SSIM}$$

where a is a weight (e.g., $\alpha$=0.5) that balances the SSIM loss and Li loss. In some cases, the two loss functions may be combined with an adjustable weight (e.g., $\alpha$).

In some cases, an attention map or mask may be added to preserve information in a particular region. For example, a lesion attention mask may be included to highlight the loss in these regions. The attention map may comprise an attention feature map or ROI attention masks. The attention map may be a lesion attention map or other attention map that comprises clinically meaningful information. For example, the attention map may comprise information about regions where particular tissues/features are located.

A lesion attention mask may be acquired automatically. In some cases, the lesion attention mask may be generated from the same fast scan SPECT image or the without requiring additional scan or source of information. For example, the lesion attention mask can be obtained based on a SUV threshold in the fast scan SPECT image. For instance, a SUV threshold may be selected and the fast scan SPECT image or input image may be filtered based on the threshold. In some cases, the filtered fast scan SPECT image may be used as the lesion attention mask. The lesion attention mask may need more accurate boundary enhancement compared to the normal structures and background. Including the lesion attention mask may beneficially preserve the quantification accuracy and/or sharpness of the features (e.g., features of lesion). The lesion attention mask can be obtained using any other suitable methods such as utilizing deep learning techniques. Below is an example of an improved lesion attention loss function:

$$\ell = L + \beta L * M$$

where B is a weight (e.g., $\beta$=100) that balances the lesion region loss and non-lesion region loss, M represents the lesion attention mask. The weight $\beta$ may be adjustable to vary the amount of information in a ROI to be taken into account during training of the model.

In some cases, the method herein may utilize deep supervision strategy in the training process to assist in the training converge. The deep supervision strategy may provide direct supervision to the hidden layers. This beneficially alleviates the problem of having gradients that "explode" or "vanish". In some cases, the total loss for training the $U^2$-Net may include the loss of the side output SPECT images and loss of the final output SPECT image. This beneficially improves the performance of the discriminator (classifier) by training the discriminative classifier using these hidden layer feature maps. Below is an example of the total loss function:

$$\mathcal{L}_{total} = \sum_{n=1}^{N} w_{side}^{(n)} \ell_{side}^{(n)} + w_{fuse} \ell_{fuse}$$

where $$\ell_{side}^{(m)}$$

is the loss of the side output SPECT (e.g., N=6, as the Sup1, Sup2, . . . , Sup6 in FIG. 2) and $\ell_{fuse}$ is the loss of the final fusion output SPECT $$S_{fuse} \cdot w_{side}^{(m)},$$

where $w_{fuse}$ control the weights of each loss term. The weight $$w_{side}^{(m)}$$

and $w_{fuse}$ may be determined based on empirical data. For example, based on the experiment data or empirical data the weight may be set as $$w_{side}^{(m)} = 0.2 \text{ and } w_{fuse} = 1.$$

The weight may be adjusted based on the empirical data automatically. Alternatively, the weight may be adjusted by a user manually.

During a training stage, the training dataset may include a pair of fast scan SPECT image, corresponding CT image and a standard SPECT image (e.g., SPECT image acquired with standard acquisition time) as ground truth data. The training data may be obtained from an imaging system (e.g., SPECT/CT scanner, SPECT scanner, CT scanner), from external data sources (e.g., clinical database, etc.) or from simulated image sets. For example, the fast scan SPECT image may be simulated low-quality SPECT images that are generated by applying different levels or types of noise to the high-quality SPECT image (i.e., ground truth data). The term "high-quality" SPECT image may also be referred to as slow-scan SPECT image or standard SPECT image which are used interchangeably throughout the specification. The term "fast scan" SPECT image may also be referred to as low-quality SPECT image or accelerated SPECT image which are used interchangeably throughout the specification. Utilizing simulated low-quality SPECT images may beneficially augment the training dataset. The image quality of the SPECT image as described herein may include general image quality, detail of radiotracer (e.g., 99mTc-MPD) distribution, presence of artifacts and/or general diagnostic confidence.

System Overview

Figure 3:
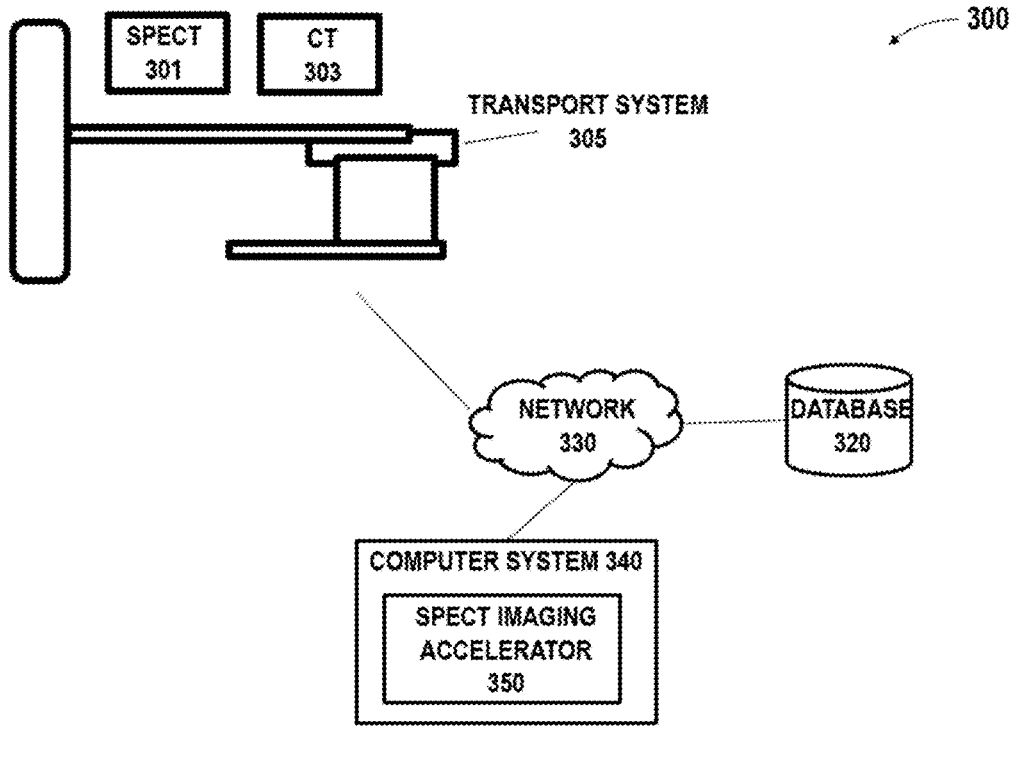
FIG. 3 schematically illustrates an example of a system implementing the method herein.

The systems and methods can be implemented on existing imaging systems such as but not limited to SPECT imaging system, CT imaging system or SPECT/CT imaging systems without a need of a change of hardware infrastructure. FIG. 3 schematically illustrates an example of a system 300 comprising a computer system 340 and one or more databases operably coupled to an imaging system over the network 330. The computer system 310 may be used for further implementing the methods and systems explained above to improve the quality of images.

As described above, a SPECT-CT imaging system combines single photon emission computed tomography (SPECT) gamma cameras and computed tomography (CT) into one imaging system. Alternatively, the imaging system may comprise separate SPECT imaging system and CT system where the SPECT and CT images are processed and combined to generate an input data. In some embodiments, the SPECT/CT imaging system may comprise a controller for controlling the operation, imaging of the two modalities (SPECT imaging module 301, CT imaging module 303) or movement of transport system 305. For example, the controller may control a CT scan based on one or more acquisition parameters set up for the CT scan and control the SPECT scan based on one or more acquisition parameters set up for the SPECT scan. The SPECT imaging module 301 may be performed by using a gamma camera to acquire multiple 2-D images (i.e., projections), from multiple angles. The controller may apply a tomographic reconstruction algorithm (e.g., filter backprojection (FBP), iterative algorithm such as algebraic reconstruction technique (ART), etc.) to the multiple projections, yielding a 3-D data set. The SPECT image may be combined with the CT image to generate the combined image as output of the imaging system. For example, reconstruction algorithms have been developed in bone hybrid imaging (SPECT/CT) scanner. Different from classic SPECT reconstructions, such reconstruction algorithms may utilize an ordered subset conjugate gradient minimization algorithm (OSCGM) for image reconstruction. This construction algorithm can provide SPECT images with bone anatomy appearance as a CT-based tissue segmentation is incorporated into SPECT reconstruction and also provide a quantitative reconstruction. Such progress of image acquisition and reconstruction could convey a higher diagnostic confidence through an enhanced bone uptake location.

The controller may be coupled to an operator console (not shown) which can include input devices (e.g., keyboard) and control panel and a display. For example, the controller may have input/output ports connected to a display, keyboard and or other IO devices. In some cases, the operator console may communicate through the network with a computer system that enables an operator to control the production and display of images on a screen of display. For example, images may be images with improved quality and/or accuracy acquired according to an accelerated acquisition scheme. For example, a user may set up the scan time for acquiring the accelerated SPECT image and/or a standard SPECT image.

The system 300 may comprise a user interface. The user interface may be configured to receive user input and output information to a user. The user input may be related to controlling or setting up an image acquisition scheme. For example, the user input may indicate scan duration (e.g., the min/bed) for each acquisition or scan time for a frame that determines one or more acquisition parameters for an accelerated acquisition scheme. The user input may be related to the operation of the SPECT/CT system (e.g., certain threshold settings for controlling program execution, image reconstruction algorithms, etc). The user interface may include a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

The system 300 may comprise computer systems and database systems 320, which may interact with a SPECT imaging accelerator 350. The computer system may comprise a laptop computer, a desktop computer, a central server, distributed computing system, etc. The processor may be a hardware processor such as a central processing unit (CPU), a graphic processing unit (GPU), a general-purpose processing unit, which can be a single core or multi core processor, or a plurality of processors for parallel processing. The processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations. The imaging platform may comprise one or more databases. The one or more databases may utilize any suitable database techniques. For instance, structured query language (SQL) or "NoSQL" database may be utilized for storing image data, raw collected data, reconstructed image data, training datasets, trained model (e.g., hyper parameters), loss function, weighting coefficients, etc. Some of the databases may be implemented using various standard data-structures, such as an array, hash, (linked) list, struct, structured text file (e.g., XML), table, JSON, NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database of the present disclosure is implemented as a data-structure, the use of the database of the present disclosure may be integrated into another component such as the component of the present disclosure. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated.

The network 330 may establish connections among the components in the imaging platform and a connection of the imaging system to external systems. The network may comprise any combination of local area and/or wide area networks using both wireless and/or wired communication systems. For example, the network may include the Internet, as well as mobile telephone networks. In one embodiment, the network uses standard communications technologies and/or protocols. Hence, the network may include links using technologies such as Ethernet, 802.11, worldwide interoperability for microwave access (WiMAX), 2G/3G/4G/5G mobile communications protocols, asynchronous transfer mode (ATM), InfiniBand, PCI Express Advanced Switching, etc. Other networking protocols used on the network can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), and the like. The data exchanged over the network can be represented using technologies and/or formats including image data in binary form (e.g., Portable Networks Graphics (PNG)), the hypertext markup language (HTML), the extensible markup language (XML), etc. In addition, all or some of links can be encrypted using conventional encryption technologies such as secure sockets layers (SSL), transport layer security (TLS), Internet Protocol security (IPsec), etc. In another embodiment, the entities on the network can use custom and/or dedicated data communications technologies instead of, or in addition to, the ones described above.

In some embodiments, the SPECT imaging accelerator may comprise multiple components, including but not limited to, a training module, an image enhancement module, and a user interface module.

The training module may be configured to train a model using the deep learning model framework as described above. The training module may train the model to predict a SPECT image with quality improved over the input low-quality SPECT. The training module may be configured to obtain and manage training datasets. For example, the training datasets for may comprise pairs of standard acquisition and shortened acquisition SPECT images, CT images and/or attention feature map from the same subject. The training module may be configured to train a deep learning network for enhancing the image quality as described elsewhere herein. The training module may be configured to implement the deep learning methods as described elsewhere herein. The training module may train a model off-line. Alternatively or additionally, the training module may use real-time data as feedback to refine the model for improvement or continual training.

The image enhancement module may be configured to enhance the SPECT image quality using a trained model obtained from the training module. The image enhancement module may implement the trained model for making inferences, i.e., outputting SPECT images with quality improved over the input fast scan SPECT image.

The user interface (UI) module may be configured to provide a UI to receive user input related to the ROI and/or user preferred output result. For instance, a user may be permitted to, via the UI, set acceleration parameters (e.g., acquisition time) or identify regions of interest (ROI) in the lower quality images to be enhanced. The UI may display the improved SPECT image.

Methods and systems of the present disclosure can be implemented by way of one or more algorithms. An algorithm can be implemented by way of software upon execution by the central processing unit.

EXPERIMENTS AND RESULTS

Figure 4:
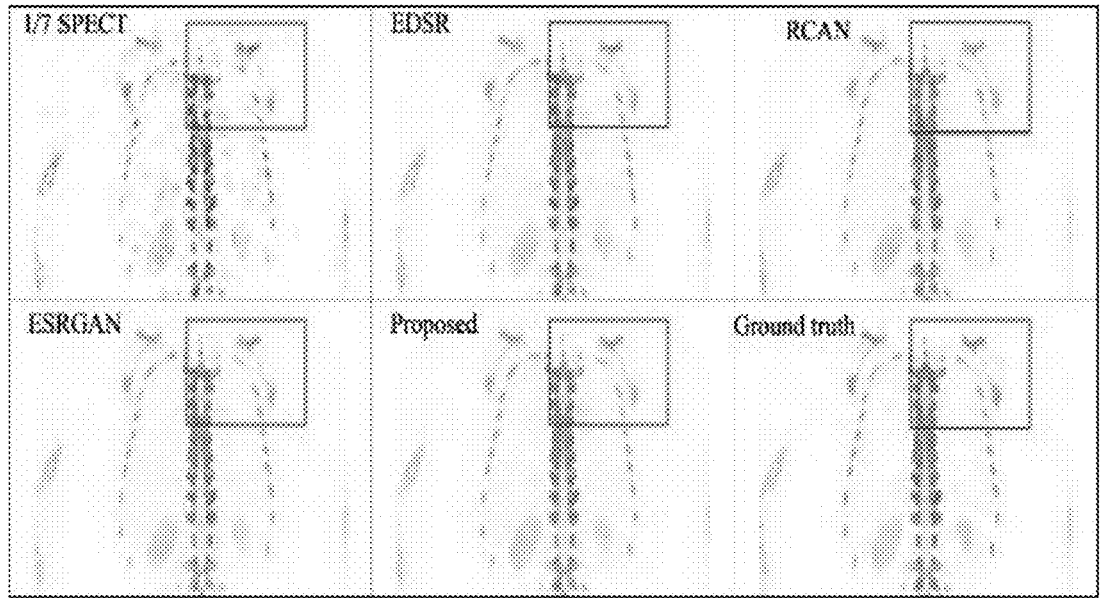
FIG. 4 and FIG. 5 show results from an experiment implementing the provided methods and systems.
Figure 5:
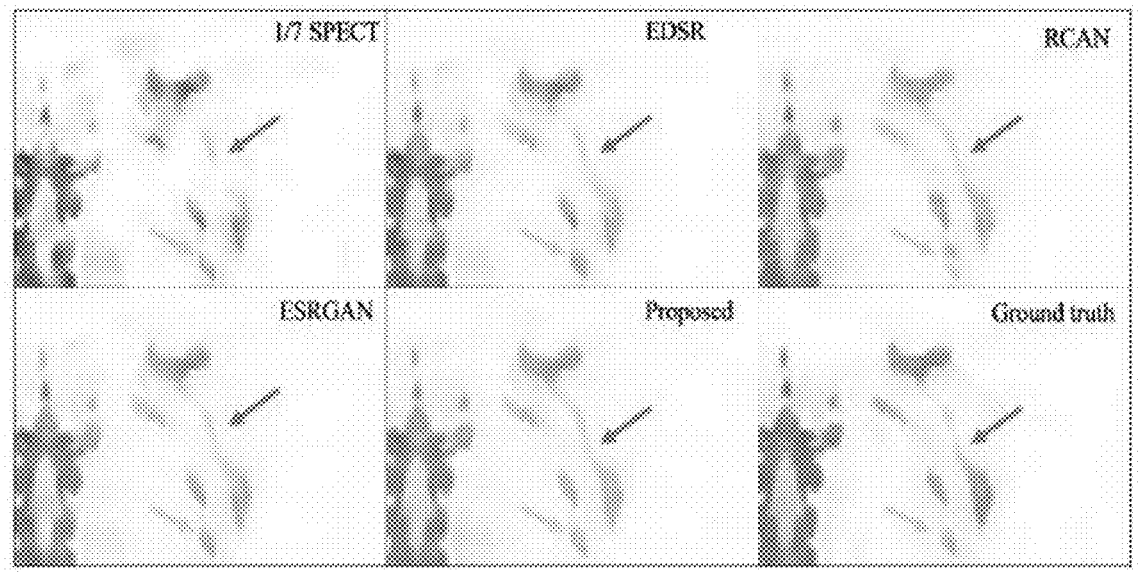

FIG. 4 and FIG. 5 show results from an experiment implementing the provided methods and systems. In the example, the clinical dataset included 30 subjects received systemic bone imaging and quantitative tomography were collected on a SPECT/CT scanner at Hospital X (Dosage of injection, 25-30 mCi). There are two scanning protocols: one standard scan with 20 seconds per frame (referred to as standard SPECT), and one fast scan with 3 seconds per frame (referred to as ⅐ SPECT). Other sampling parameters were as follows: 60 frames, single probe rotated 180°, single rotation 6°. SPECT projection data were reconstructed using ordered subset conjugate gradient (OSCG) algorithm. 20 subjects were used for training the proposed deep learned model while the rest 10 subjects were set for testing the synthesized result.

Implementation details: the provided method is implemented in PyTorch 1.6.0 and trained on a deep learning GPU workstation. The experiment set 100 epochs for the training stage and batch size is set to 4 by using axial slice as inference plane. Optimizer and learning rate are selected (e.g., learning rate is set to 0.0002) for training both the generator and the discriminator (classifier) networks and divided by 10 after 80 epochs.

Quantitative Evaluation Method

The method herein may also be capable of quantitatively evaluating the model performance or quality of the synthesized SPECT image. For example, quantitative image quality metrics such as normalized root-mean-squared-error (NRMSE), peak signal to noise ratio (PSNR), and structural similarity (SSIM) may be calculated for the enhanced and non-enhanced accelerated SPECT scans, where higher image quality is represented by higher PSNR and/or SSIM. The proposed deep learning model is also compared with other widely-used deep learning image enhancement methods (e.g., EDSR, RCAN and ESRGAN) respectively to demonstrate the performance of the provide model. As shown in the below table, the proposed method has superior performance compared to other methods.

TABLE 1

Average PSNR and SSIM comparing with state-of-the-art methods.

|  | ⅐ SPECT | EDSR [14] | RCAN [15] | ESRGAN [16] | Proposed |
|---|---|---|---|---|---|
| SSIM | 0.765 | 0.778 | 0.781 | 0.772 | 0.788 |
| PSNR | 37.7 | 38.6 | 40.5 | 40.1 | 40.8 |

Visualization results for comparison with different methods are shown in FIG. 4. A zoomed-in region is also provided for better comparison in FIG. 5. Quantitative results ARE presented in the above Table. In general, the result of the present disclosure outperforms the other competitive methods on both qualitative and quantitative evaluation.

The noise in the chest region as shown in the ⅐ SPECT image has been successfully removed in the synthesized SPECT image (labeled as proposed in the figure) generated by the presented method. This improvement is achieved by using $U^2$-Net as the neural network architecture since it provides abundant contextual information from different scales for improving the anatomical structural details, as well as including CT image as the input of network to provide the clear anatomy features. The provided method also increases the sharpness with consistent details and achieves the highest PSNR and SSIM score at the same time. As shown in the table, the synthesized standard SPECT images generated by the provided method have the highest evaluation metrics (PSNR=40.8, SSIM=0.788).

Clinical Assessment

Figure 6:
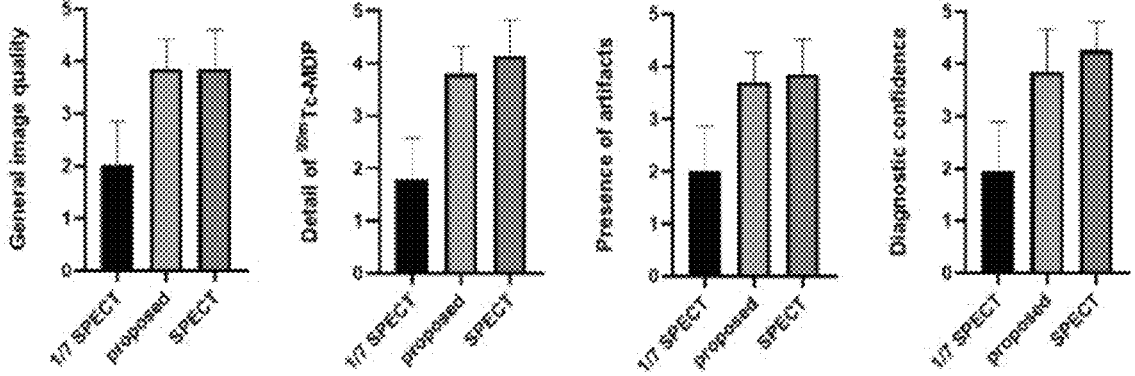
FIG. 6 shows an example of qualitative results from an experiment.

Two readers independently grade ⅐ SPECT, synthesized SPECT by the provided DeepSPECT method and standard SPECT in terms of general image quality, detail of 99mTc-MPD distribution, presence of artifacts and general diagnostic confidence. The grade is set from 1 to 5 (5 is the highest score). Detailed results are shown in FIG. 6. The synthesized SPECT image is shown to have the same general image quality and detail of 99mTc-MPD distribution compared with standard SPECT. The synthesized SPECT images are significantly better than the fast SPECT image with respect to presence of artifacts and general diagnostic confidence.

Ablation Study

Figure 7:
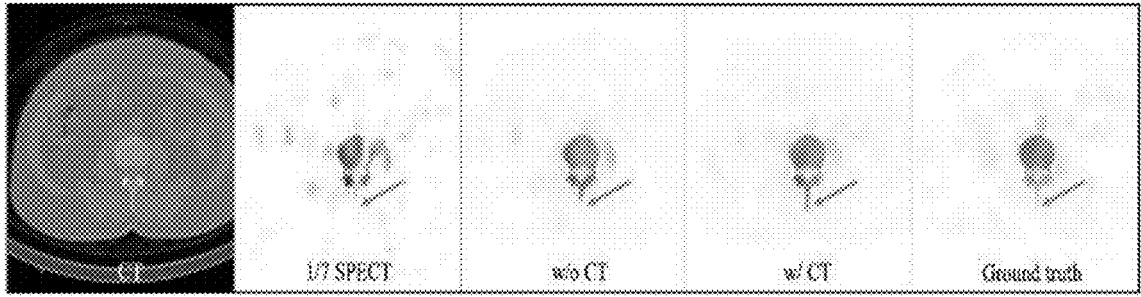
FIG. 7 shows visual results of with and without CT image as input.
Figure 8:
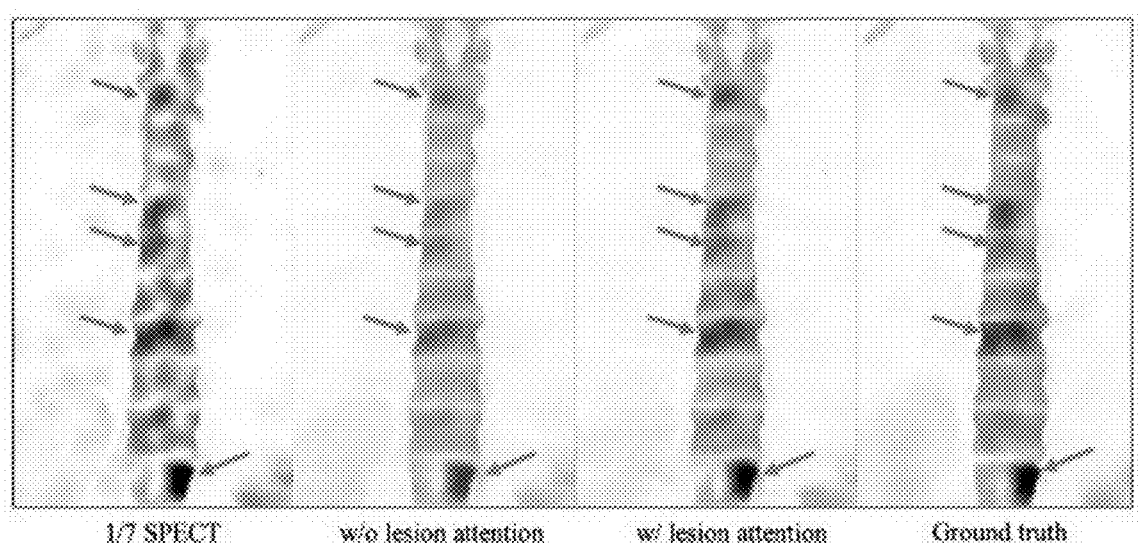
FIG. 8 shows visual results of with and without using lesion attention.

To verify the effectiveness of using both SPECT and CT images (e.g., ⅐ SPECT and CT image) as input for boosting the image quality, results obtained with and without CT images are compared. The results are shown in FIG. 7 in which the bone structure pointed by blue arrow has been clearly recovered in the result with both ⅐ SPECT and CT as input, while the result without CT as input fails to recover this bone structure due to the missing information in the original ⅐ SPECT image. The effectiveness of using lesion attention loss is demonstrated in FIG. 8. It is shown that the synthesized SPECT using lesion attention has more accurate SUV values and better contrast compared to the SPECT images without lesion attention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for improving image quality comprising:
  (a) acquiring, using single-photon emission computed tomography (SPECT), a first medical image of a subject, wherein the first medical image is acquired with shortened acquisition time;
  (b) combining the medical image acquired using SPECT with a second medical image acquired using computed tomography (CT) to generate a multi-modal input image; and
  (c) applying a deep learning network model to the multi-modal input image and outputting an enhanced medical image, wherein the enhanced medical image has an image quality same as a SPECT image acquired with an acquisition time longer than the shortened acquisition time combined with a corresponding CT image or has a quantification accuracy improved over the first medical image, and wherein the deep learning network model comprises a $U^2$-Net architecture including a plurality of residual blocks with different sizes to provide contextual information at different scales.

2. The computer-implemented method of claim 1, wherein an output generated by a decoder stage of the $U^2$-Net architecture is fused with the multi-modal input image to generate the enhanced medical image.

3. The computer-implemented method of claim 1, wherein the deep learning network model is trained using training data comprising a SPECT image acquired using shortened acquisition time, a corresponding CT image and a SPECT image acquired using a standard acquisition time.

4. The computer-implemented method of claim 1, wherein the quantification accuracy is improved by training deep learning network model using a lesion attention mask.

5. The computer-implemented method of claim 4, wherein the lesion attention mask is included in a loss function of the deep learning network model.

6. The computer-implemented method of claim 4, wherein the lesion attention mask is generated from a SPECT image acquired using shortened acquisition time in the training data.

7. The computer-implemented method of claim 6, wherein the lesion attention mask is generated by filtering the SPECT image acquired using shortened acquisition time with a standardized uptake value (SUV) threshold.

8. The computer-implemented method of claim 1, wherein the first medical image and the second medical image are acquired using a SPECT/CT scanner.

9. The computer-implemented method of claim 1, wherein the enhanced medical image has an improved signal-noise ratio.

10. A non-transitory computer-readable storage medium including instructions that, when executed by one or more processors, cause the one or more processors to perform operations comprising:
  (a) acquiring, using single-photon emission computed tomography (SPECT), a first medical image of a subject, wherein the first medical image is acquired with shortened acquisition time;
  (b) combining the medical image acquired using SPECT with a second medical image acquired using computed tomography (CT) to generate a multi-modal input image; and
  (c) applying a deep learning network model to the multi-modal input image and outputting an enhanced medical image, wherein the enhanced medical image has an image quality same as a SPECT image acquired with an acquisition time longer than the shortened acquisition time combined with a corresponding CT image or has a quantification accuracy improved over the first medical image, and wherein the deep learning network model comprises a $U^2$-Net architecture including a plurality of residual blocks with different sizes to provide contextual information at different scales.

11. The non-transitory computer-readable storage medium of claim 10, wherein an output generated by a decoder stage of the $U^2$-Net architecture is fused with the multi-modal input image to generate the enhanced medical image.

12. The non-transitory computer-readable storage medium of claim 10, wherein the deep learning network model is trained using training data comprising a SPECT image acquired using shortened acquisition time, a corresponding CT image and a SPECT image acquired using a standard acquisition time.

13. The non-transitory computer-readable storage medium of claim 10, wherein the quantification accuracy is improved by training deep learning network model using a lesion attention mask.

14. The non-transitory computer-readable storage medium of claim 13, wherein the lesion attention mask is included in a loss function of the deep learning network model.

15. The non-transitory computer-readable storage medium of claim 13, wherein the lesion attention mask is generated from a SPECT image acquired using shortened acquisition time in the training data.

16. The non-transitory computer-readable storage medium of claim 15, wherein the lesion attention mask is generated by filtering the SPECT image acquired using shortened acquisition time with a standardized uptake value (SUV) threshold.

17. The non-transitory computer-readable storage medium of claim 10, wherein the first medical image and the second medical image are acquired using a SPECT/CT scanner.

18. The non-transitory computer-readable storage medium of claim 10, wherein the enhanced medical image has an improved signal-noise ratio.

* * * * *